United States Patent

Yoshimoto et al.

[11] 4,062,896
[45] * Dec. 13, 1977

[54] NITRO-DIPHENYL ETHERS

[75] Inventors: Takeo Yoshimoto; Keiichi Igarashi, both of Yokohama; Takeo Harayama, Kamakura; Masaaki Ura, Yokohama; Teruhiko Toyama, Fujisawa; Osamu Morikawa, Chigasaki; Yoshio Takasawa, Chigasaki; Yoshikata Hojo, Chigasaki, all of Japan

[73] Assignee: Mitsui Toatsu Chemicals, Incorporated, Tokyo, Japan

[*] Notice: The portion of the term of this patent subsequent to July 13, 1993, has been disclaimed.

[21] Appl. No.: 515,316

[22] Filed: Oct. 16, 1974

[30] Foreign Application Priority Data

Dec. 19, 1973   Japan .................................. 48-141331

[51] Int. Cl.$^2$ ............................................. C07C 43/22
[52] U.S. Cl. ................................... 260/613 R; 71/124
[58] Field of Search ................................... 260/613 R

[56] References Cited

U.S. PATENT DOCUMENTS

| | | | |
|---|---|---|---|
| 2,988,571 | 6/1961 | MacFie et al. | 260/613 R |
| 3,294,847 | 12/1966 | Albright et al. | 260/613 R X |
| 3,376,281 | 4/1968 | Cox et al. | 260/613 D X |
| 3,562,335 | 2/1971 | Gildersleve | 260/613 R |
| 3,776,961 | 12/1973 | Theissen | 260/613 R |
| 3,798,276 | 3/1974 | Bayer | 260/612 R |
| 3,849,503 | 11/1974 | Shigehara et al. | 260/613 R |
| 3,969,102 | 7/1976 | Yoshimoto et al. | 260/613 R X |

Primary Examiner—Bernard Helfin
Attorney, Agent, or Firm—Lane, Aitken, Dunner & Ziems

[57] ABSTRACT

Nitrodiphenyl ether derivatives of the general formula:

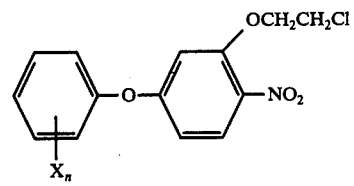

wherein X stands for Cl, F, $CH_3$ or $CF_3$, $n$ is an integer of 1–3 with the proviso that X may be the same or different when $n$ is 2 or 3 but $X_n$ should not be 2,4-dichloro substituent, are valuable as herbicides possessing an excellent herbicidal activity to a wide variety of undesirable weeds with an extremely low toxicity to useful crops. These nitrodiphenyl ether derivatives are prepared by hydroxyethylation of a compound of the above general formula except that a halogen atom is present in place of nitro group and subsequent halogenation of the β-hydroxyethoxy group of the resulting compound.

6 Claims, No Drawings

NITRO-DIPHENYL ETHERS

BACKGROUND OF THE INVENTION

This invention relates to new compounds of diphenyl ether series possessing a very strong herbicidal activity, a process for preparing same and a herbicide comprising the new compounds as active ingredient.

Many compounds of diphenyl ether series have been examined hitherto to determine their effects in practical use as herbicides. In many cases, the presence or absence, degree, mode of function, selectivity and duration of the herbicidal activities of these compounds are markedly variable according to even a slight difference in chemical structure of these compounds such as sort, number and position of substituents thereof. Thus, it is extremely difficult to estimate the herbicidal activity of these compounds from their similarity in chemical structure.

It is a well-known fact that some compounds of diphenyl ether series are excellent herbicides. For example, 2,4-dichloro-4'-nitrodiphenyl ether (referred to hereinafter as NIP) and 2,4,6-trichloro-4'-nitrodiphenyl ether (referred to hereinafter as CNP) are widely used as herbicides in rice fields.

Ideal herbicides are required to exhibit on one hand a very strong herbicidal activity to undesirable plants even at a low level concentration and on the other hand an extremely low toxicity to useful plants. However, herbicides developed hitherto still fail to meet fully either or both of these requirements. In recent years, a problem of environmental pollution has also arisen in the field of agricultural agents and the use of a highly effective compound in a small amount is recommended to minimize any harmful side effect of the compound. Under these circumstances, there is a great demand for developing a new type herbicide which fully meets the aforesaid requirements.

BRIEF SUMMARY OF THE INVENTION

Accordingly, it is an object of this invention to provide a new class of diphenyl ether compounds possessing a very strong herbicidal activity with a slight toxicity to useful plants.

It is another object of this invention to provide a process for the preparation of the new class of diphenyl ether compounds.

It is still another object of this invention to provide a herbicide comprising a new diphenyl ether compound as active ingredient.

It is further object of this invention to provide a method of controlling growth of plants by applying the herbicide to plants or soil.

These and other objects, features and advantages of this invention will appear more fully as the description proceeds.

DETAILED DESCRIPTION OF THE INVENTION

We have made many researches made for developing new compounds with a strong herbicidal activity by synthetizing various compounds of diphenyl ether series and examining their herbicidal activity. As a result of these researches, it has now been found that a certain class of diphenyl ether compounds exhibit excellent herbicidal characteristics and fully meets the aforesaid requirements.

In accordance with this invention, there is provided a new class of diphenyl ether compounds of the general formula:

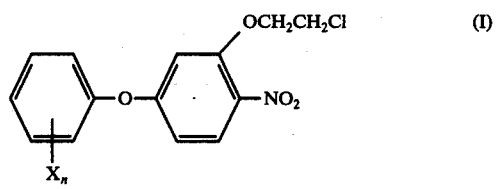

wherein X stands for Cl, F, $CH_3$ or $CF_3$ and $n$ is an integer of 1–3 with the proviso that X may be the same or different when $n$ is 2 or 3 but $X_n$ should not be 2,4-dichloro substituent.

These new compounds are generally light yellow crystalline substance and may be purified by way of recrystallization from an organic solvent such as a lower alcohol or by way of distillation under reduced pressure.

Illustrative of the new compounds of this invention are:
2,4,6-trichloro-3'-($\beta$-chloroethoxy)-4'-nitrodiphenyl ether (mp 99°–100.5° C)
2,4-dichloro-6-fluoro-3'-($\beta$-chloroethoxy)-4'-nitrodiphenyl ether (mp 60°–62° C)
2,4-dichloro-6-methyl-3'-($\beta$-chloroethoxy)-4'-nitrodiphenyl ether (mp 95°–96° C)
2-methyl-4-chloro-3'-($\beta$-chloroethoxy)-4'-nitrodiphenyl ether (mp 89°–91° C)
4-chloro-3-($\beta$-chloroethoxy)-4'-nitrodiphenyl ether (mp 109°–111° C)
3-methyl-3'-($\beta$-chloroethoxy)-4'-nitrodiphenyl ether (mp 58°–61° C)
3-trifluoromethyl-3'-($\beta$-chloroethoxy)-4'-nitrodiphenyl ether (mp 92°–93° C)
2-chloro-3-trifluoromethyl-3'-($\beta$-chloroethoxy)-4'-nitrodiphenyl ether.

These new diphenyl ether compounds can be prepared by a simple two-step reaction which comprises first condensing a compound of the general formula:

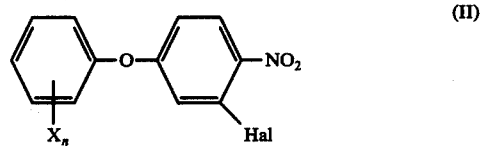

wherein X and $n$ have the same meanings as given above and Hal stands for a halogen atom, with ethylene glycol in the presence of an acid-binding agent and then chlorinating the hydroxyethoxy group of the resulting condensate. A series of these reactions are known and can be carried out in a usual manner adopted for hydroxyalkylation of halogen atoms and halogenation of $\beta$-hydroxyalkoxy groups. For example, the condensation reaction in the first step is carried out by reacting a starting material of the above general formula with ethylene glycol at an elevated temperature in the presence of a suitable acid-binding agent optionally with a liquid vehicle. Illustrative of the acid-binding agent are caustic alkali such as potassium hydroxide or sodium hydroxide, alkali metal carbonates such as sodium carbonate and sodium bicarbonate, and tertiary amines such as triethylamine and pyridine. Preferred examples of the liquid vehicle include water, organic solvents miscible with water such as lower alcohols and a mixture thereof. The reaction is preferably carried out at an elevated temperature up to a reflux temperature of the mixture. Chlorination of the hydroxyethoxy group in the intermediately formed 3'-hydroxyethoxy compound is carried out by warming this compound with an adequate chlorinating agent such as thionyl chloride or dry hydrogen chloride in a suitable solvent. The use of thionyl chloride is preferred because of its easiness in handling and reactivity. The end product is purified, for example, by recrystallization from an alcohol but may be used directly as active ingredient for the herbicide.

The resulting product may be used alone as the herbicide of this invention, but in general, it is dissolved in or dispersed into an appropriate liquid vehicle such as an organic solvent, or alternatively mixed with or adsorbed to an appropriate inert solid carrier such as diluent or weighing agent. The herbicides may be used in various forms such as emulsion, wettable agent, pellet, powder etc., if necessary by incorporating the herbicides with various assistants such as emulsifier, stabilizer, dispersing agent, suspending agent, vehicle, wetting agent and permeating agent. Preferred examples of the liquid vehicle include alcohols, naphtha, and aliphatic and aromatic hydrocarbons while preferred examples of the inert solid carrier include mineral powders such as talc, bentonite, etc. and insoluble inorganic compounds such as calucium carbonate, silica, etc.

The herbicides of this invention may contain a mixture of at least two active ingredients and may be used in combination with one or more other substances such as agricultural agents including other kinds of herbicides, insecticides, sterilizers and plant growth controlling agents, soil-improving agents and fertilizers. It is also possible to manufacture preparations containing the herbicides of this invention in combination with these agricultural agents. Examples of other kinds of herbicides which may be used jointly with the herbicides of this invention may include those of urea series, thiolcarbamate series, organophosphorus series, acid amide series, triazine series and aryloxyfatty acid series.

The concentration of the active ingradients in the herbicide of this invention is preferably 1–10% in the case of granules 40–80% in the case of wettable agents and 10–50% in the case of emulsion (all the percentages are by weight).

In comparison with NIP or CNP, the active ingredients of this invention exhibit excellent herbicidal activity to barnyard grass and other kinds of weeds. The herbicidal activity is scarcely weakened when the active ingredients are diluted to a low concentration. In addition, the active ingredients of this invention exhibit a prolonged durability in herbicidal activity and have little harmful effects upon useful crops.

This invention will now be explained in more detail by way of Examples wherein all of the parts and percentage are by weight.

EXAMPLE 1: Preparation of the new β-chloroethoxy-nitrodiphenyl ethers a. 2,4,6-trichloro-3'-(β-chloroethoxy)-4'-nitrodiphenyl ether In a 300 ml flask equipped with a stirrer, a thermometer, a condenser and an inlet for starting materials were placed 100 ml of ethylene glycol and 3.8 g of potassium hydroxide (85% solid) (0.058 mole). The mixture was warmed to dissolve the potassium hydroxide in the ethylene glycol. The solution was cooled to room temperature, and 20 g of finely pulverized 2,3',4,6-tetrachloro-4'-nitrodiphenyl ether (0.057 mole) were added within a short period of time to the solution under agitation. The inner temperature of the flask was maintained at 90° C by externally warming it and the reaction was continued for 6 hours. The reaction mixture was cooled to room temperature and poured into 200 ml of water whereby an oily substance was precipitated which was then extracted with 300 ml of benzene. The benzene phase was washed with 200 ml of a 5% aqueous solution of sodium hydroxide and then with water thoroughly until the aqueous phase became neutral. The benzene phase was allowed to stand stationarily and then separated. After dehydration of the benzene phase with anhydrous sodium sulfate, benzene was removed by evaporation under reduced pressure whereby 18 g of a viscous oily substance were obtained. This substance was composed predominantly of 2,4,6-trichloro-3'-(β-hydroxyethoxy)-4'-nitrodiphenyl ether.

The oily substance was dissolved in 100 ml of benzene and was placed in a 300 ml flask equipped with a stirrer, a thermometer, an inlet for starting materials and a condenser with a gas-absorbing apparatus at one end thereof. The inner temperature was maintained at 60° C and 15 g of thionyl chloride were added dropwise over about 30 minutes to the mixture under agitation. The reaction was continued for 4 hours under agitation at the same temperature. After transfer of the reaction mixture to an evaporation flask, benzene and excess thionyl chloride were removed by evaporation under reduced pressure whereupon 17 g of a crystalline residue were obtained. The crystalline residue was dissolved in a tenfold volume of ethanol by warming and cooled to 10° C to effect recrystallization whereby 11 g of 2,4,6-trichloro-3'-(β-chloroethoxy)-4'-nitrodiphenyl ether (Compound 1) were obtained which was light yellow crystals (m.p. 99°–100.5° C). Elementary analysis as $C_{14}H_9Cl_4NO_4$

|  | C (%) | H (%) | N (%) | Cl (%) |
|---|---|---|---|---|
| calc. | 42.35 | 2.28 | 3.53 | 35.72 |
| found | 42.50 | 2.32 | 3.44 | 35.52 | b. Compounds represented by the general formula (I) other than Compound 1 can also be prepared according to the method illustrated above by replacing 2,3',4,6-tetrachloro-4'-nitro-diphenyl ether by the corresponding starting material. Typical other compounds (Compounds 2–8) and their characteristics are tabulated in Table A.

Table A

General formula:

(phenyl)$_{X_n}$—O—(phenyl with OCH$_2$CH$_2$Cl and NO$_2$)

| Compound No. | X$_n$ substituent | M.P. (B.P.) °C | \multicolumn{5}{c}{Elementary analysis Found/(Calc.)} |
|---|---|---|---|---|---|---|---|

| Compound No. | X$_n$ | M.P. (B.P.) °C | O | H | N | Cl | F |
|---|---|---|---|---|---|---|---|
| 2 | 2,4-Cl, F | 60 – 62 (196–200/0.5mmHg) | 44.23 (44.15 | 2.37 2.36 | 3.70 3.68 | 27.84 27.99 | 4.99 4.81) |
| 3 | 2,4-Cl, CH$_3$ | 95 – 96 (222–230/1mmHg) | 47.95 (47.81 | 3.34 3.19 | 3.92 3.72 | 28.26 28.29) | |
| 4 | Cl, CH$_3$ | 89– 91 | 52.46 (52.65 | 3.58 3.83 | 3.94 4.09 | 20.77 20.72 | |
| 5 | Cl | 109 – 111 | 51.03 (51.22 | 3.56 3.35 | 4.10 4.27 | 21.73 21.65) | |
| 6 | CH$_3$ | 58 – 61 | 58.43 (58.54 | 4.39 4.59 | 4.54 4.44 | 11.18 11.52) | |
| 7 | CF$_3$ | 92 – 93 (180–185/1.5mmHg) | 49.92 (49.79 | 3.00 3.04 | 3.76 3.87 | 10.08 9.82 | 15.50 15.76) |
| 8 | Cl, CF$_3$ | | 45.61 (45.48 | 2.70 2.54 | 3.40 3.54 | 18.00 17.90 | 14.28 14.39) |

EXAMPLE 2: Granular preparation 1

7 Parts of Compound 1, 70 parts of bentonite, 20 parts of talc 2 parts of sodium dodecylbenzenesulfonate and 1 part of sodium ligninesulfonate were mixed and kneaded with an appropriate amount of water. The mixture was shaped into granules by a usual method using a pelletizer whereby 100 parts of a granular preparation were obtained.

EXAMPLE 3: Granular preparation 2

One part of Compound 2, 80 parts of bentonite, 17 parts of talc, 1 part of polyoxyechyleneglycol monolaurate and one part of sodium naphthalenesulfonate were mixed and kneaded with an appropriate amount of water. The mixture was then shaped into granules by a usual method using an extruding pelletizer whereby 100 parts of a granular preparation were prepared.

EXAMPLE 4: Wettable agent 1

50 Parts of Compound 3, 40 parts of talc, 7 parts of sodium laurylsulfate, and 3 parts of sodium alkylnaphthalenesulfornate were mixed and then pulverized to prepare 100 parts of a wettable agent.

EXAMPLE 5: Wettable agent 2

70 Parts of Compound 6, 20 parts of diatomaceous earth and 10 parts of sodium dodecylbenzenesulfonate were mixed and then pulverized to prepare 100 parts of a wettable agent.

EXAMPLE 6: Emulsions

10 Parts of Compound 2, 10 parts of solvol 800 A (an emulsifier manufactured by Toyo Chemicals, Co., Ltd.) and 80 parts of solvent naphtha were mixed to prepare 100 parts of a stock solution for emulsion.

that in the untreated area, the herbicidal effect was classified into 6 grades, "0" being no suppression of growth and "5" being perfect suppression of growth. (the herbicidal effect was evaluated in the same manner also in Table 2 et seq.)

Table 1

| Compound tested | Amount used (Active ingredient g/a) | Rice | Soy-bean | Maize | Crab-grass | Barn-yard grass | Lambs quarters | Redroot pigweed |
|---|---|---|---|---|---|---|---|---|
| Compound 1 | 10 | 0 | 0 | 0 | 5 | 4 | 4 | 4 |
|  | 20 | 0 | 0 | 0 | 5 | 5 | 5 | 5 |
|  | 50 | 1 | 0 | 1 | 5 | 5 | 5 | 5 |
| Compound 2 | 5 | 0 | 0 | 0 | 5 | 5 | 5 | 5 |
|  | 10 | 0 | 0 | 0 | 5 | 5 | 5 | 5 |
|  | 20 | 1 | 0 | 1 | 5 | 5 | 5 | 5 |
| Compound 3 | 10 | 0 | 0 | 0 | 4 | 4 | 4 | 4 |
|  | 20 | 0 | 0 | 0 | 5 | 5 | 4 | 5 |
|  | 50 | 0 | 0 | 0 | 5 | 5 | 5 | 5 |
| Compound 8 | 5 | 0 | 0 | 0 | 5 | 5 | 5 | 5 |
|  | 10 | 0 | 0 | 0 | 5 | 5 | 5 | 5 |
|  | 20 | 1 | 1 | 0 | 5 | 5 | 5 | 5 |
| NIP E.C. (Comparative) | 10 | 0 | 0 | 0 | 2 | 2 | 3 | 2 |
|  | 20 | 1 | 0 | 0 | 3 | 3 | 4 | 3 |
|  | 50 | 2 | 1 | 1 | 4 | 5 | 4 | 4 |
| CNP E.C. (Comparative) | 10 | 0 | 0 | 0 | 1 | 1 | 2 | 1 |
|  | 20 | 1 | 0 | 0 | 3 | 2 | 3 | 2 |
|  | 50 | 1 | 1 | 1 | 4 | 4 | 4 | 3 |

EXAMPLE 7: Evaluation of herbicidal effect 3.5 Kg of an air-dried fine soil (which passed through a sieve of 14 mesh) in a crop farm were placed in a/5000 Wagner pot, to which one gram each of N, $P_2O_5$, $K_2O$ was evenly added in the form of chemical fertilizers. The water content in the soil was regulated to 60% of the maximum capacity for water and then the soil was sown with a definite quantity of seeds of crops to be tested. The seeds were covered with the soil. An emulsion of a compound to be tested was prepared according to the method described in Example 6 and a given amount of the emulsion was diluted with water in an amount of 10 liters per acre. The soil in the pot was evenly treated with the diluted emulsion by the aid of a pippette and then allowed to stand in a greenhouse to permit growth of the crops.

One month after the treatment the state of growth of the crops and the emergence of weeds was observed and the results tabulated in Table 1 were obtained. In comparison of the state of growth of the crops or the state of emergence of weeds in the treated areas with

EXAMPLE 8: Evaluation of herbicidal effect 3.3 Kg of an air-dried soil (which passed through a sieve of 14 mesh) in a rice field including seeds of common rice field weeds in a naturally mixed state were placed in a/5000 Wagner pot, to which 0.8 g each of N, $P_2O_5$ and $K_2O$ was evenly added in form of chemical fertilizers. The soil was mixed with an appropriate amount of water, and the level of the water was maintained above that of the soil. Three rice seedlings (2.0 leaf stages) which had been grown in a greenhouse were planted in the pot and were grown in a greenhouse. The weeds began to sprout five days after the transplantation of rice. Then, a given amount of a compound to be tested was added in the form of a wettable agent prepared according to the method described in Example 4 or 5 to the pot where the level of water was maintained above that of the soil.

One month after the treatment, the state of growth of rice and weeds was observed and the results tabulated in Table 2 were obtained. During the test period, the depth of water in the pots were at all times maintained at 3 cm.

Table 2

| Compound tested | Amount used (Active ingredient g/a) | Rice | Barnyardgrass (Echinochloa crus-galli) | Other common weeds Broad-leaved* | Narrow-leaved** |
|---|---|---|---|---|---|
| Compound 1 | 5 | 0 | 5 | 5 | 5 |
|  | 10 | 0 | 5 | 5 | 5 |
|  | 20 | 0 | 5 | 5 | 5 |
| Compound 2 | 1 | 0 | 5 | 5 | 5 |
|  | 2 | 0 | 5 | 5 | 5 |
|  | 5 | 1*** | 5 | 5 | 5 |
| Compound 3 | 5 | 0 | 5 | 5 | 5 |
|  | 10 | 0 | 5 | 5 | 5 |
|  | 20 | 0 | 5 | 5 | 5 |
| Compound 4 | 5 | 0 | 3 | 4 | 4 |
|  | 10 | 0 | 5 | 5 | 5 |
|  | 20 | 0 | 5 | 5 | 5 |
| Compound 5 | 5 | 0 | 2 | 4 | 4 |
|  | 10 | 0 | 4 | 5 | 5 |
|  | 20 | 0 | 5 | 5 | 5 |
| Compound 6 | 5 | 0 | 2 | 4 | 4 |
|  | 10 | 0 | 3 | 4 | 4 |
|  | 20 | 0 | 5 | 5 | 5 |
| Compound 8 | 1 | 0 | 5 | 5 | 5 |
|  | 2 | 0 | 5 | 5 | 5 |
|  | 5 | 1 | 5 | 5 | 5 |
| NIP E.C. (Comparative) | 5 | 0 | 1 | 2 | 2 |
|  | 10 | 1*** | 2 | 3 | 3 |
|  | 20 | 2*** | 4 | 4 | 4 |

Table 2-continued

| Compound tested | Amount used (Active ingredient g/a) | Rice | Barnyardgrass (Echinochloa crus-galli) | Other common weeds Broad-leaved* | Narrow-leaved** |
| --- | --- | --- | --- | --- | --- |
| CNP E.C. (Comparative) | 5 | 0 | 1 | 2 | 1 |
|  | 10 | 1*** | 2 | 3 | 3 |
|  | 20 | 1*** | 4 | 4 | 4 |

Notes:
*Monochoria vaginalis, Water plantain Alisma canaliculatum
**Umbrella sedge Cyperus difformis, Spike rush Eleocharis acicularis
***Leaf sheaths and leaf blades turned brown due to the phytotoxicity of the compound EXAMPLE 9: Evaluation of herbicidal effect 3.3 Kg of an air-dried soil (which passed through a sieve of 14 mesh) in a rice field including seeds of common rice field weeds in a naturally mixed state were placed in a/5000 Wagner pot, to which 0.8 g each of N, P₂O₅ and K₂O was evenly added in the form of chemical fertilizers. The soil was mixed with an appropriate amount of water, and the level of the water was maintained above that of the soil. A given amount of a compound to be tested was added in the form of an emulsion prepared according to the method described in Example 6 to the pot where the compound was homogeneously mixed with the soil up to the depth of 5 cm, or alternatively the emulsion was added dropwise by the aid of a pippette to the water covering the soil. Three rice seedlings (3.0 leaf stages) were planted in the pot where the depth of water covering the soil was 3 cm. The seedlings were allowed to grow in a greenhouse.

One month after the treatment, any influence of the compound on rice and the state of emergence or growth of weeds were observed and the results are shown in Table 3.

Table 3

| Compound tested | Amount used (Active ingredient g/a) | Incorporated into the soil in a depth of 5 cm | | | | Applied on the soil surface directly after puddling | | | |
| --- | --- | --- | --- | --- | --- | --- | --- | --- | --- |
|  |  | Rice | Barnyard-grass Echinochloa crus-galli | Broad-* leaved | Narrow-** leaved | Rice | Barnyard-grass Echinochloa crus-galli | Broad-* leaved | Narrow-** leaved |
| Compound 1 | 5 | 0 | 5 | 5 | 5 | 0 | 5 | 5 | 5 |
|  | 10 | 0 | 5 | 5 | 5 | 0 | 5 | 5 | 5 |
|  | 20 | 0 | 5 | 5 | 5 | 0 | 5 | 5 | 5 |
| Compound 2 | 1 | 0 | 5 | 5 | 5 | 0 | 5 | 5 | 5 |
|  | 2 | 0 | 5 | 5 | 5 | 0 | 5 | 5 | 5 |
|  | 5 | 0 | 5 | 5 | 5 | 1 | 5 | 5 | 5 |
| Compound 3 | 5 | 0 | 4 | 4 | 4 | 0 | 5 | 5 | 4 |
|  | 10 | 0 | 5 | 5 | 5 | 0 | 5 | 5 | 5 |
|  | 20 | 0 | 5 | 5 | 5 | 0 | 5 | 5 | 5 |
| Compound 8 | 1 | 0 | 5 | 5 | 5 | 0 | 5 | 5 | 5 |
|  | 2 | 0 | 5 | 5 | 5 | 0 | 5 | 5 | 5 |
|  | 5 | 0 | 5 | 5 | 5 | 0 | 5 | 5 | 5 |
| NIP E.C. (Comparative) | 5 | 0 | 1 | 1 | 1 | 1*** | 2 | 2 | 2 |
|  | 10 | 1*** | 2 | 3 | 2 | 2*** | 3 | 3 | 4 |
|  | 20 | 2*** | 4 | 4 | 4 | 3*** | 4 | 4 | 4 |
| CNP E.C. (Comparative) | 5 | 0 | 1 | 1 | 1 | 0 | 1 | 1 | 1 |
|  | 10 | 1*** | 2 | 3 | 2 | 1*** | 2 | 3 | 3 |
|  | 20 | 2*** | 3 | 4 | 3 | 2*** | 4 | 4 | 4 |

Notes: The items marked with *,  and * are same as in the case of Table 2.

EXAMPLE 10:

Three days after plantation of rice seedlings, the rice field was divided into areas of 10 m². Granules of a compound to be tested were prepared according to the method described in Example 2 or 3 and sprinkled in an amount of 300 g per acre into the water covering the soil. Thirty days after the treatment, the state of emergence of weeds per 1 m² of the test areas and any phytotoxicity to rice plant were observed and investigated. The results are shown in Table 4.

Table 4

| Compound tested | Content (%) in the tested granular preparation | Amount used (Active ingredient g/a) | Phytotoxicity to rice | Weight of weeds (air dried weight g/a) | | | | |
| --- | --- | --- | --- | --- | --- | --- | --- | --- |
|  |  |  |  | Barnyard grass Echinochloa crus-galli | Monochoria vaginalis | Umbrella sedge Cyperus difformis | Bulrush Scirpus juncoides | Spike rush Eleocharis acicularis |
| Compound 1 (5% granular agent) | 5 | 15 | None | 0 | 0 | 0 | 0 | 0 |
| Compound 2 (1% granular agent) | 1 | 3 | Slight*** | 0 | 0 | 0 | 0 | 0 |
| Compound 3 (7% granular agent) | 7 | 21 | None | 0.2 | 0 | 0 | 1 | 0 |
| Compound 4 (7% granular agent) | 7 | 21 | None | 4 | 2 | 1 | 1 | 2 |
| Compound 5 | 9 | 27 | None | 7 | 2 | 0.4 | 2 | 2 |
| Compound 7 | 9 | 27 | None | 7 | 2 | 0.4 | 2 | 2 |
| Compound 8 | 1.5 | 4.5 | None | 0 | 0 | 0 | 0 | 0 |
| NIP Granules (Comparative) |  | 21 | Moderate*** | 37 | 19 | 8 | 31 | 10 |
| CNP Granules |  | 27 | Small*** | 39 | 12 | 4 | 29 | 8 |

Table 4-continued

| Compound tested | Content (%) in the tested granular preparation | Amount used (Active ingredient g/a) | Phyto- toxicity to rice | Weight of weeds (air dried weight g/a) | | | | |
| --- | --- | --- | --- | --- | --- | --- | --- | --- |
| | | | | Barnyard grass Echinochloa crus-galli | Monochoria vaginalis | Umbrella sedge Cyperus difformis | Bulrush Scirpus juncoides | Spike rush Eleocharis acicularis |
| (Comparative) Untreated | | None | | 140 | 47 | 29 | 41 | 25 |

Note:
***Same as in the case of Table 2

As is evident from the results of these tests, the herbicide of this invention not only exhibits a very strong herbicidal activity against various undesirable weeds but also has better characteristics than the conventional herbicides of diphenyl ether series in that the lowering of the activity upon dilution is slight and the toxic effect on various useful crops is absent.

What is claimed is:
1. 2,4-Dichloro-6-fluoro-3'-($\beta$-chloroethoxy)-4'-nitrodiphenyl ether.
2. 2,4-Dichloro-6-methyl-3'-($\beta$-chloroethoxy)-4'-nitrodiphenyl ether.
3. 2-Methyl-4-chloro-3'-($\beta$-chloroethoxy)-4'-nitrodiphenyl ether.
4. 3-Methyl-3'-($\beta$-chloroethoxy)-4'-nitrodiphenyl ether.
5. 3-Trifluoromethyl-3'-($\beta$-chloroethoxy)-4'-nitrodiphenyl ether.
6. 2-chloro-4-trifluoromethyl-3'-($\beta$-chloroethoxy)-4'-nitrodiphenyl ether.

* * * * *